(12) United States Patent
Dan et al.

(10) Patent No.: US 11,953,498 B2
(45) Date of Patent: Apr. 9, 2024

(54) IMAGE PROCESSING DEVICE, IMAGE PROCESSING METHOD, PROGRAM, AND EVALUATION METHOD

(71) Applicant: NIKON CORPORATION, Tokyo (JP)

(72) Inventors: Tomoro Dan, Yokohama (JP); Hiroaki Kii, Fujisawa (JP); Takayuki Uozumi, Machida (JP); Yasujiro Kiyota, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 418 days.

(21) Appl. No.: 17/227,967

(22) Filed: Apr. 12, 2021

(65) Prior Publication Data
US 2021/0301246 A1  Sep. 30, 2021

Related U.S. Application Data

(63) Continuation of application No. PCT/JP2019/039250, filed on Oct. 4, 2019.

(30) Foreign Application Priority Data

Oct. 12, 2018 (JP) .................................. 2018-193814

(51) Int. Cl.
G06T 7/11 (2017.01)
C12M 1/34 (2006.01)
(Continued)

(52) U.S. Cl.
CPC ......... *G01N 33/5073* (2013.01); *C12M 41/36* (2013.01); *C12Q 1/04* (2013.01);
(Continued)

(58) Field of Classification Search
CPC ..... G01N 33/5073; C12M 41/36; C12Q 1/04; G06T 7/0016; G06T 7/11;
(Continued)

(56) References Cited

U.S. PATENT DOCUMENTS

2012/0114219 A1* 5/2012 Nakagawa ........... G02B 21/367
382/133
2012/0315620 A1* 12/2012 Watakabe .......... G01N 33/5073
435/286.2
(Continued)

FOREIGN PATENT DOCUMENTS

EP 2457989 A1 5/2012
EP 2487249 A1 8/2012
(Continued)

OTHER PUBLICATIONS

Jan. 7, 2019 International Search Report issued in International Patent Application No. PCT/JP2019/039250.
(Continued)

*Primary Examiner* — Said M Elnoubi
(74) *Attorney, Agent, or Firm* — Oliff PLC

(57) ABSTRACT

An image processing device includes: a processor; and a memory encoded with instructions executed by the processor, including: imaging pluripotent stem cells with time in a culture process and acquiring a plurality of images, extracting a colony region of the cells from the image, extracting a high luminance region on the basis of a group of pixels with larger luminance values than a standard value from among pixels constituting the image, extracting an extraction target region with relatively high contrast in the colony region on the basis of the colony and high luminance regions, and outputting the extraction target region as an extraction result, wherein as a relationship among the colony, high luminance, and extraction target regions, the colony region is formed, the high luminance region is then formed therein, and the extraction target region is then formed in the high luminance region in the culture process of the cells.

14 Claims, 12 Drawing Sheets

(51) Int. Cl.
*C12Q 1/04* (2006.01)
*G01N 33/50* (2006.01)
*G06T 7/00* (2017.01)

(52) U.S. Cl.
CPC .............. *G06T 7/0016* (2013.01); *G06T 7/11* (2017.01); *G06T 2207/10056* (2013.01); *G06T 2207/30024* (2013.01); *G06T 2207/30242* (2013.01)

(58) Field of Classification Search
CPC . G06T 2207/10056; G06T 2207/30024; G06T 2207/30242; G06T 7/155
See application file for complete search history.

(56) References Cited

U.S. PATENT DOCUMENTS

2017/0159003 A1 6/2017 Shimase et al.
2017/0199171 A1* 7/2017 Kiyota ................. G06V 20/698

FOREIGN PATENT DOCUMENTS

| | | |
|---|---|---|
| EP | 3156477 A1 | 4/2017 |
| WO | 2011/010449 A1 | 1/2011 |
| WO | 2011/043077 A1 | 4/2011 |
| WO | 2015/193951 A1 | 12/2015 |
| WO | 2016/013394 A1 | 1/2016 |

OTHER PUBLICATIONS

Jan. 7, 2019 Written Opinion of the International Searching Authority issued in International Patent Application No. PCT/JP2019/039250.
Jan. 7, 2020 International Search Report issued in International Patent Application No. PCT/JP2019/039250.
Jan. 7, 2020 Written Opinion of the International Searching Authority issued in International Patent Application No. PCT/JP2019/039250.
Jun. 22, 2022 extended Search Report issued in European Patent Application No. 19871996.5.
Nov. 29, 2023 Office Action issued in Chinese Patent Application No. 201980067104.5.

* cited by examiner

IMAGE PROCESSING DEVICE, IMAGE PROCESSING METHOD, PROGRAM, AND EVALUATION METHOD

TECHNICAL FIELD

The present invention relates to an image processing device, an image processing method, a program, and an evaluation method.

Priority is claimed on Japanese Patent Application No. 2018-193814, filed Oct. 12, 2018, the content of which is incorporated herein by reference.

BACKGROUND ART

Cells that form colonies such as induced pluripotent stem cells (iPS cells) gradually change from a state in which colonies are immature to a matured state. Since a larger number of iPS cells are required for regenerative medicine and the like, a process of cultivating cells and raising the number of cells is required. A process of raising the number of iPS cells is called an extended culture process. In the extended culture process, a passage timing is determined on the basis of a colony maturity level. Although the maturity level is determined by operators visually checking the sizes of cells in a colony in the related art, variations may occur depending on each operator.

In order to curb variations in passage culture timing depending on each operator, a device that automatically performs operations of collecting cells after expansion culture, producing a cell suspension, measuring the number of cells per unit amount of cell suspension, diluting the cell suspension to a desired cell concentration on the basis of the measurement result, and subculturing the cells has been proposed (Patent Document 1). However, the device described in Patent Document 1 peels the cells off of a culture vessel, collects the cells in a collection bag, measures and adjusts the number of cells, and performs passage culture, and it is thus not possible to determine whether a colony has been sufficiently matured, and in a case in which the colony has not been sufficiently matured, it is not possible to continue the culture to mature the colony. A method that enables determination of maturity directly from a colony that is being adhesively cultured is required.

CITATION LIST

Patent Literature

Patent Document 1

PCT International Publication No. 2016/013394

SUMMARY OF INVENTION

In order to solve the aforementioned problem, according to an aspect of the present invention, there is provided an image processing device including: a processor; and a memory encoded with instructions executed by the processor, wherein the instructions causing the processor to perform operations including: imaging pluripotent stem cells with time in a culture process of the pluripotent stem cells and acquiring a plurality of images, extracting a colony region of the pluripotent stem cells from the image, extracting, from the image, a high luminance region that is a region on the basis of a group of pixels with larger luminance values than a standard value from among pixels constituting the image, extracting an extraction target region with relatively high contrast in the colony region from the image on the basis of the colony region and the high luminance region, and outputting the extraction target region as an extraction result, wherein as a relationship among the colony region, the high luminance region, and the extraction target region, the colony region is formed, the high luminance region is then formed in the colony region, and the extraction target region is then formed in the high luminance region in the culture process of the pluripotent stem cells.

In order to solve the aforementioned problem, according to an aspect of the present invention, there is provided an image processing device including: a processor; and a memory encoded with instructions executed by the processor, wherein the instructions causing the processor to perform operations including: imaging pluripotent stem cells with time in a culture process of the pluripotent stem cells and acquiring a plurality of images, extracting a colony region of the pluripotent stem cells from the image, extracting, from the image, a focused region that is a region on the basis of a group of pixels with luminance values exceeding a standard value from among pixels constituting the image, extracting an extraction target region with relatively high contrast in the colony region from the image on the basis of the colony region and the focused region, and outputting the extraction target region as an extraction result, wherein as a relationship among the colony region, the focused region, and the extraction target region, the colony region is formed, the focused region is then formed in the colony region, and the extraction target region is then formed in the focused region in the culture process of the pluripotent stem cells.

In order to solve the aforementioned problem, according to an aspect of the present invention, there is provided an evaluation method for evaluating maturity of a colony of pluripotent stem cells, the method including: an acquisition process of acquiring a phase contrast image of the colony; a detection process of detecting a striated structure including pixels with high luminance in the phase contrast image; and an output process of outputting an analysis result of maturity of the colony on the basis of a temporal change in the striated structure detected in the detection process.

DESCRIPTION OF EMBODIMENTS

First Embodiment

Figure 1:
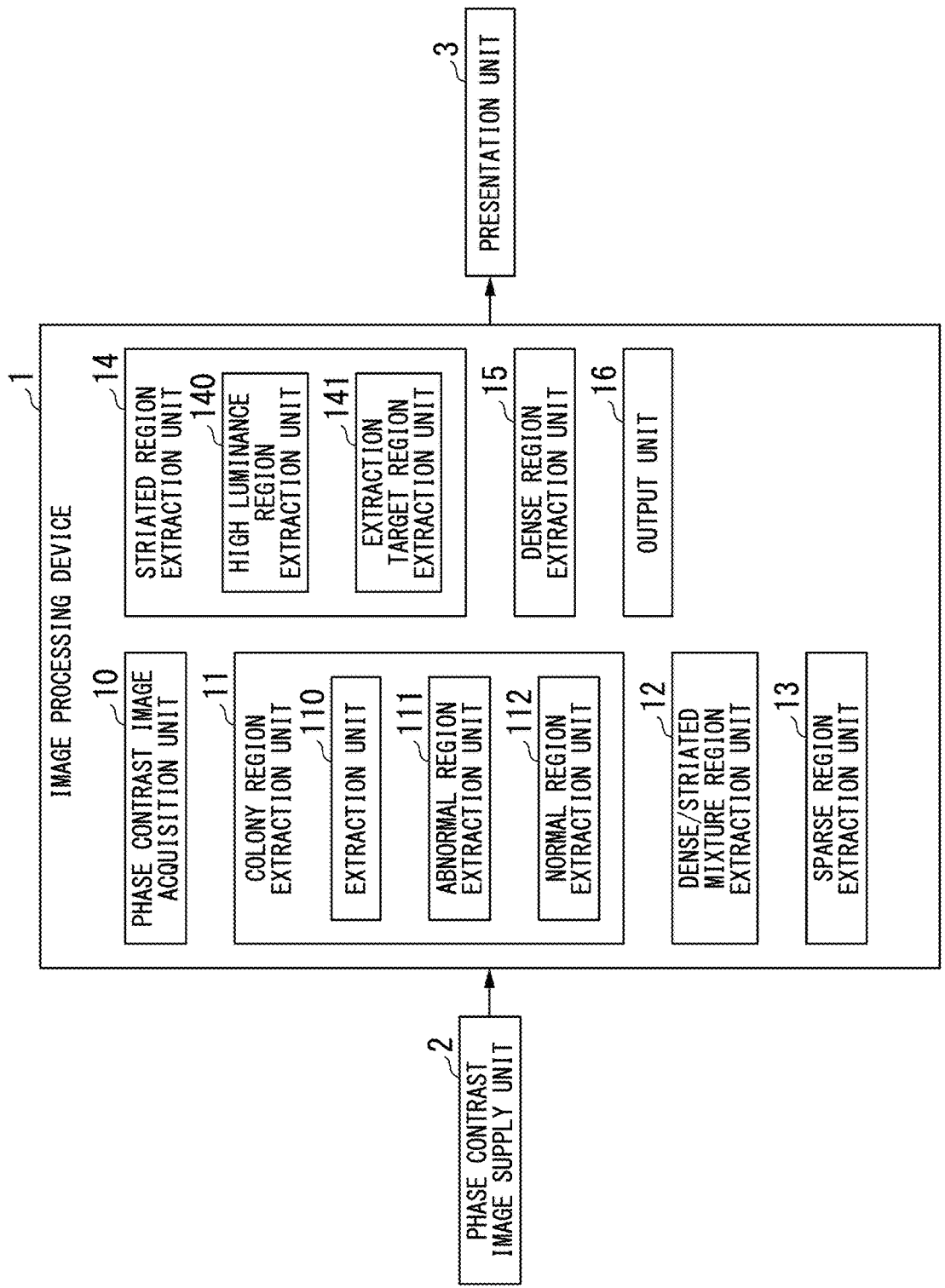
FIG. 1 is a diagram illustrating an example of an image processing device according to a first embodiment of the present invention.

Hereinafter, embodiments of the present invention will be described in detail with reference to the drawings. FIG. 1 is a diagram illustrating an example of an image processing device 1 according to the present embodiment. The image processing device 1 extracts an extraction target region that is a region that is a target for extraction from a captured phase contrast image P0 of pluripotent stem cells. Here, the pluripotent stem cells are stem cells capable of differentiating into all cell types belonging to three germ layers, namely endoderm, mesoderm, and ectoderm, and examples thereof include iPS cells and embryonic stem cells (ES cells).

In the present embodiment, the extraction target region is a region where a striated pattern appears in the phase contrast image P0. In order to explain the striated pattern here, a culture process of the pluripotent stem cells, which are iPS cells, will be described.

A colony of the pluripotent stem cells, which are iPS cells, changes from an unformed state to a matured state through an immature state in a culture process.

The colony unformed state is a state in which there is a single cell as a pluripotent stem cell and a colony has not been formed. In the colony immature state, a colony has been formed, but an area per cell is large, and cell density is low. Hereinafter, a region where cell density is low will also be referred to as a sparse region.

The matured state is, for example, a state in which the colony is suitable for passage. In the colony in the matured state, the area per cell has become small, and the cell density has increased. Hereinafter, a region where the cell density is high will also be referred to as a dense region. In the colony in the matured state, a dense region has been formed at the center, and a sparse region surrounds the surroundings of the dense region.

As an intermediate state between the colony immature state and the matured state, there is a transition state. The transition state is a state in which the pluripotent stem cells have formed a colony but the colony has not been sufficiently matured.

In the transition state, a striated region is seen in the phase contrast image of the colony. The striated region is a region in which a plurality of elongated striated patterns can be seen in the phase contrast image. The region is considered to look striated because contrast of gaps of a plurality of pluripotent stem cells increases as a result of the pluripotent stem cells becoming dense with maturing of the colony.

In the transition state, the colony includes the striated region, the dense region that surrounds the surroundings of the striated region, and the sparse region that surrounds the surroundings of the dense region.

The image processing device 1 includes a phase contrast image acquisition unit a colony region extraction unit 11, a dense/striated mixture region extraction unit 12, a sparse region extraction unit 13, a striated region extraction unit 14, a dense region extraction unit 15, and an output unit 16.

The phase contrast image acquisition unit 10 acquires the phase contrast image P0 supplied from a phase contrast image supply unit 2. Here, the phase contrast image P0 is an example of a microscopic image obtained using transmitted illumination. The phase contrast image P0 is an image obtained by capturing pluripotent stem cells by converting a phase difference of transmitted light of an illumination light applied to the pluripotent stem cells into a light-dark difference. The phase contrast image P0 is, for example, an image in which an enlarged image of the pluripotent stem cells obtained by a phase contrast microscope is captured.

The microscope images by transmitted illumination may be, for example, differential interference images, quantitative phase images, or the like, in addition to the phase contrast images.

The colony region extraction unit 11 extracts a colony region CR of pluripotent stem cells from the phase contrast image P0 acquired by the phase contrast image acquisition unit 10. Here, the colony region extraction unit 11 includes an extraction unit 110, an abnormal region extraction unit 111, and a normal region extraction unit 112.

The extraction unit 110 extracts the colony region CR of the pluripotent stem cells from the phase contrast image P0 and generates a colony mask CM. The colony mask CM is a mask image that masks a region other than the colony region CR in the phase contrast image P0.

The abnormal region extraction unit 111 extracts an abnormal region AR from the colony region CR extracted by the extraction unit 110. The abnormal region AR is a region formed by abnormal cells departing from the state of the pluripotent stem cells in the colony region CR. Here, although it is important to culture the pluripotent stem cells while maintaining the pluripotent state in the culture of the pluripotent stem cells, abnormal cells departing from the state of the pluripotent stem cells may appear in the culture process.

The normal region extraction unit 112 extracts a normal region NR and generates a normal region mask NM from the colony region CR extracted by the extraction unit 110. The normal region NR is a region formed by normal cells that maintain the state of the pluripotent stem cells in the colony region CR. The normal region mask NM is a mask image that masks a region other than the normal region NR in the phase contrast image P0.

The dense/striated mixture region extraction unit 12 extracts a dense/striated region MSR and generates a dense/striated mask MSM on the basis of the phase contrast image P0 acquired by the phase contrast image acquisition unit 10, the colony mask CM generated by the extraction unit 110, and the normal region mask NM generated by the normal region extraction unit 112. Here, the dense/striated region MSR is a region including both the dense region DR and the striated region SR. The dense/striated mask MSM is a mask image that masks a region other than the dense/striated region MSR in the phase contrast image P0.

The sparse region extraction unit 13 generates a sparse mask PM on the basis of the dense/striated mask MSM generated by the dense/striated mixture region extraction unit 12 and the normal region mask NM generated by the normal region extraction unit 112. The sparse mask PM is a mask image that masks a region other than the sparse region PR in the phase contrast image P0.

The striated region extraction unit 14 extracts the striated region SR and generates a striated mask SM on the basis of the phase contrast image P0 acquired by the phase contrast image acquisition unit 10 and the dense/striated mask MSM generated by the dense/striated mixture region extraction unit 12. The striated mask SM is a mask image that masks a region other than the striated region SR in the phase contrast image P0.

Here, the striated region extraction unit 14 includes a high luminance region extraction unit 140 and an extraction target region extraction unit 141.

The high luminance region extraction unit 140 extracts a high luminance region HR from the phase contrast image P0 acquired by the phase contrast image acquisition unit 10. Here, the high luminance region HR is a region based on a group of pixels with larger luminance values than a standard value from among pixels constituting the phase contrast image P0. The high luminance region HR includes a group of pixels with larger luminance values than the standard value and surroundings of the group of the pixels.

The extraction target region extraction unit 141 extracts an extraction target region from the high luminance region HR extracted by the high luminance region extraction unit 140 on the basis of the dense/striated mask MSM generated by the dense/striated mixture region extraction unit 12.

The extraction target region is the striated region SR in the phase contrast image P0 in one example. Here, the striated region SR is a region where a striated pattern appears in the phase contrast image P0 as described above. In other words, the extraction target region is a region where the striated pattern appears in the phase contrast image P0.

The dense region extraction unit 15 extracts a dense region DR and generates a dense mask DM on the basis of the dense/striated mask MSM generated by the dense/striated mixture region extraction unit 12 and the striated mask SM generated by the striated region extraction unit 14.

The output unit 16 outputs a processing result PP to a presentation unit 3 and causes the presentation unit 3 to display the processing result PP. The processing result PP is, for example, an image in which the striated region SR extracted by the striated region extraction unit 14, the dense region DR extracted by the dense region extraction unit 15, and the sparse region PR extracted by the sparse region extraction unit 13 are indicated in the phase contrast image P0. The processing result PP may be information indicating the striated region SR extracted by the striated region extraction unit 14, information indicating the dense region DR extracted by the dense region extraction unit and information indicating the sparse region PR extracted by the sparse region extraction unit 13.

Note that the output unit 16 may output the processing result PP to an output device other than the presentation unit 3, a storage device, or the like.

The phase contrast image supply unit 2 supplies the phase contrast image P0 to the image processing device 1.

The presentation unit 3 presents the presentation result PP supplied from the image processing device 1. The presentation unit 3 is, for example, a display device such as a display.

Figure 2:
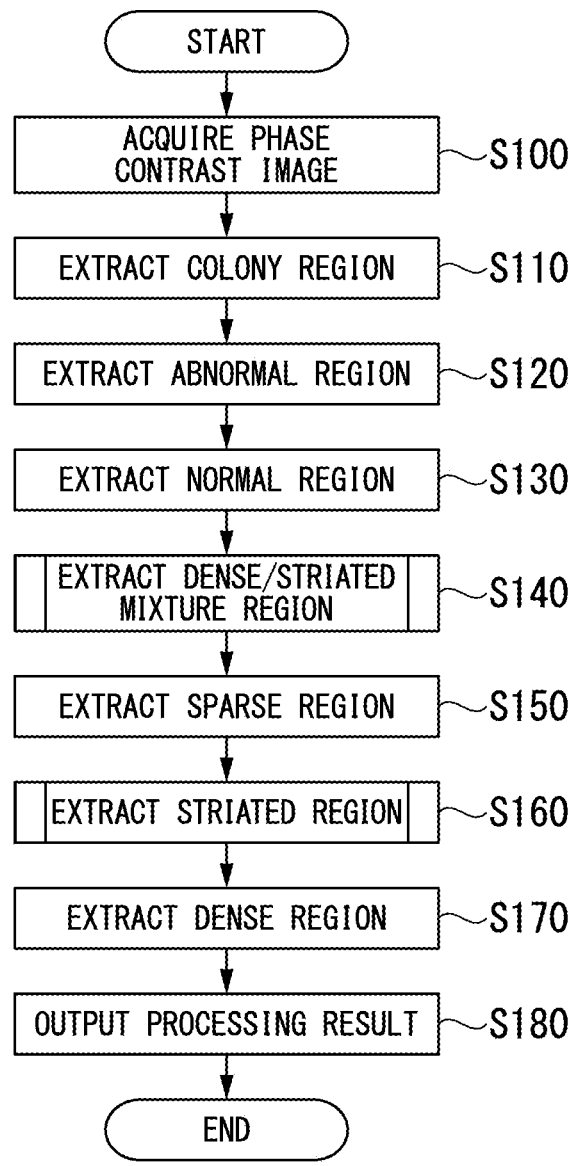
FIG. 2 is a diagram illustrating an example of extraction target region extraction processing of an image processing device according to the first embodiment of the present invention.

FIG. 2 is a diagram illustrating an example of extraction target region extraction processing of the image processing device 1 according to the present embodiment.

In the following description, addition of another image to one image means generation of an image including pixels with luminance as a result of adding, to luminance of pixels in the one image, luminance of pixels in the other image corresponding to the pixels.

Also, subtraction of another image from one image means generation of an image including pixels with luminance as a result of subtracting, from luminance of pixels in the one image, luminance of pixels in the other image corresponding to the pixels.

Also, in a case in which logical AND of one image and another image is employed, the luminance of the pixels in an image obtained as a result of employing the logical AND has a value other than zero only in a case in which both the luminance of the pixels in the one image and the luminance of the pixels in the other image corresponding to the pixels are not zero.

Step S100: The phase contrast image acquisition unit 10 acquires a phase contrast image P1 supplied from the phase contrast image supply unit 2. The phase contrast image P1 is an example of the phase contrast image P0. The phase contrast image acquisition unit 10 supplies the acquired phase contrast image P1 to the colony region extraction unit 11, the dense/striated mixture region extraction unit 12, and the striated region extraction unit 14.

Here, the phase contrast image P1 will be described with reference to FIG. 3.

Figure 3:
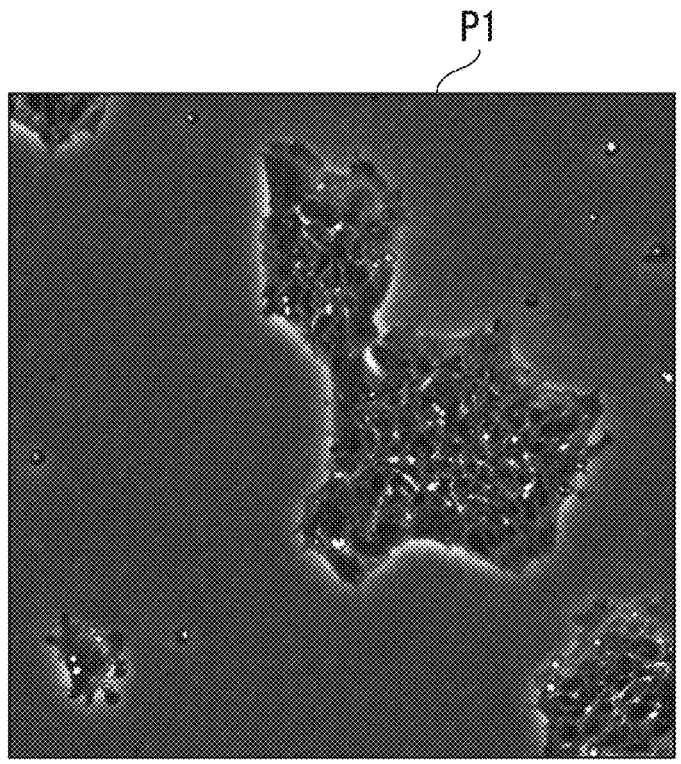
FIG. 3 is a diagram illustrating an example of a phase contrast image according to the first embodiment of the present invention.

FIG. 3 is a diagram illustrating an example of the phase contrast image P1 according to the present embodiment. The phase contrast image P1 is a captured image of a colony of pluripotent stem cells.

Returning to FIG. 2, extraction processing of the image processing device 1 will be continued.

Step S110: The extraction unit 110 of the colony region extraction unit 11 extracts the colony region CR of the pluripotent stem cells from the phase contrast image P1 acquired by the phase contrast image acquisition unit 10.

Here, the extraction unit 110 extracts a cell region that is a region where the cells are imaged from the phase contrast image P1 before extracting the colony region CR of the pluripotent stem cells. The extraction unit 110 extracts the cell region from the phase contrast image P1 on the basis of known edge detection in one example.

The extraction unit 110 extracts the colony region CR from the extracted cell region. The extraction unit 110 extracts a cell region that is wider than a predetermined area as the colony region CR, for example. The extraction unit 110 generates the colony mask CM on the basis of the extracted colony region CR. The extraction of the colony region CR is not limited to the method in which the extraction is performed on the basis of the area of the cell region and can be performed by various known methods.

The extraction unit 110 supplies the generated colony mask CM to the abnormal region extraction unit 111 and the normal region extraction unit 112. Also, the extraction unit 110 supplies the generated colony mask CM to the dense/striated mixture region extraction unit 12.

Here, the colony mask CM will be described with reference to FIG. 4.

Figure 4:
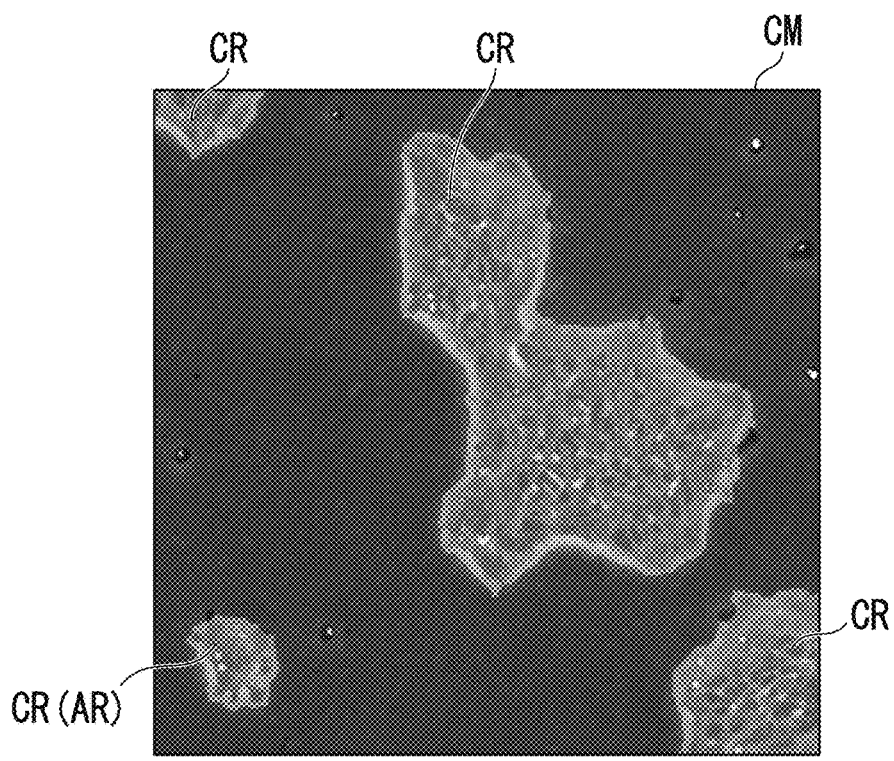
FIG. 4 is a diagram illustrating an example of a colony mask according to the first embodiment of the present invention.

FIG. 4 is a diagram illustrating an example of the colony mask CM according to the present embodiment. In FIG. 4, a region other than the colony region CR in the phase contrast image P1 is masked by the colony mask CM.

Returning to FIG. 2, description of extraction processing of the image processing device 1 will be continued.

Step S110: The abnormal region extraction unit 111 extracts the abnormal region AR from the colony region CR extracted by the extraction unit 110. Here, the abnormal region extraction unit 111 extracts the abnormal region AR on the basis of the phase contrast image P1 acquired by the phase contrast image acquisition unit 10 and the colony mask CM generated by the extraction unit 110. The abnormal region extraction unit 111 can extract the abnormal region AR from the colony region CR on the basis of presence/absence of halo in the surroundings, for example, although the extraction may be performed by any method as long as abnormal cells other than the pluripotent stem cells are extracted.

A halo is a portion of a phase contrast image in which a phase difference between one region and another region is large, and as a result, a brightness is higher than the surroundings at a boundary between the one region and the other region. The colonies of normal pluripotent stem cells have many halos around them, and the colonies of abnormal cells have few halos around them.

Therefore, the normal region NR can be defined as a region with surroundings including a portion in which the phase difference is equal to or greater than a predetermined value in the colony region CR. The abnormal region AR can be defined as a region with surroundings not including a portion in which the phase difference is equal to or greater than the predetermined value in the colony region CR.

The abnormal region extraction unit 111 extracts, as the abnormal region AR, the partial region with surroundings not including halo in the colony region CR. The abnormal region extraction unit 111 supplies information indicating the extracted abnormal region AR to the normal region extraction unit 112.

Step S130: The normal region extraction unit 112 extracts the normal region NR and generates the normal region mask NM from the colony region CR extracted by the extraction unit 110.

Here, the normal region extraction unit 112 excludes the abnormal region AR from the colony region CR extracted by the extraction unit 110 on the basis of the colony mask CM generated by the extraction unit 110 and the information indicating the abnormal region AR extracted by the abnormal region extraction unit 111. The normal region extraction unit 112 extracts, as the normal region NR, a region remaining after excluding the abnormal region AR from the colony mask CM.

In the present embodiment, the normal region extraction unit 112 is included in the colony region extraction unit 11. In another embodiment, the colony region extraction unit 11 may directly extract, as the normal region NR, a region with surroundings including a portion where the phase contrast is equal to or greater than a predetermined value in the colony region CR without performing the process of extracting the abnormal region AR.

The normal region extraction unit 112 generates the normal region mask NM as a result of extracting the normal region NR. The normal region extraction unit 112 supplies the generated normal region mask NM to the dense/striated mixture region extraction unit 12 and the sparse region extraction unit 13.

Here, the normal region mask NM will be described with reference to FIG. 5.

Figure 5:
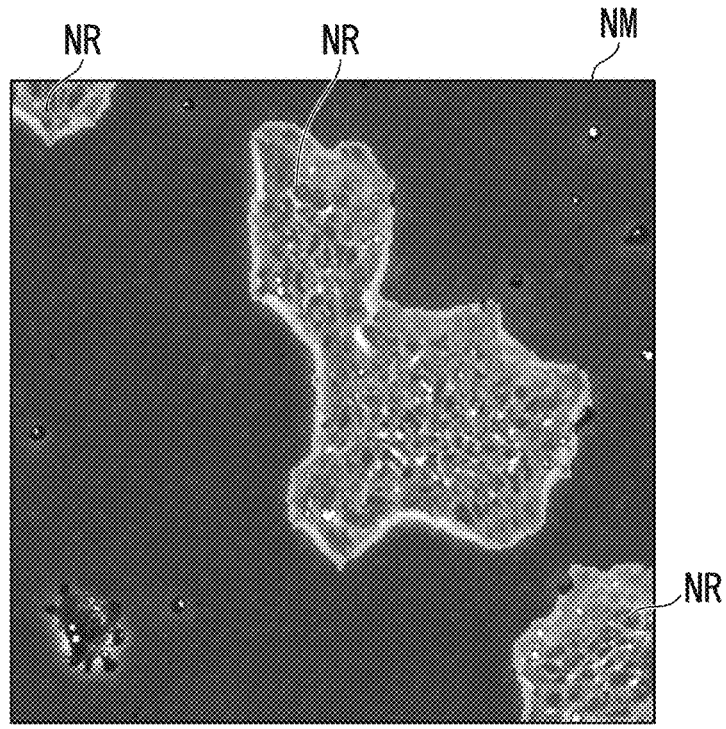
FIG. 5 is a diagram illustrating an example of a normal region mask according to the first embodiment of the present invention.

FIG. 5 is a diagram illustrating an example of the normal region mask NM according to the present embodiment. In FIG. 5, a region other than the normal region NR in the phase contrast image P1 is masked by the normal region mask NM.

Returning to FIG. 2, description of the extraction processing of the image processing device 1 will be continued.

Step S140: The dense/striated mixture region extraction unit 12 extracts the dense/striated region MSR on the basis of the phase contrast image P1 acquired by the phase contrast image acquisition unit 10, the colony mask CM generated by the extraction unit 110, and the normal region mask NM generated by the normal region extraction unit 112.

Returning to FIGS. 6 and 7 here, dense/striated region extraction processing that is processing in which the dense/striated mixture region extraction unit 12 extracts the dense/striated region MSR will be described.

Figure 6:
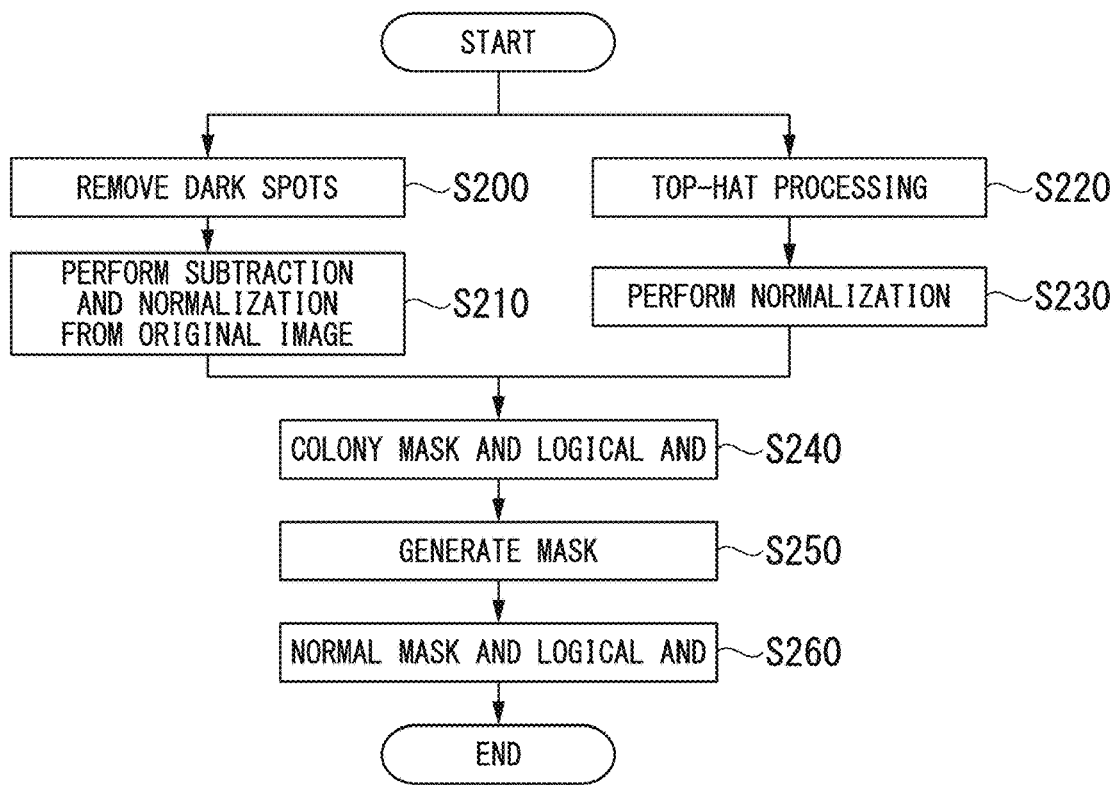
FIG. 6 is a diagram illustrating an example of dense/striated region extraction processing according to the first embodiment of the present invention.

FIG. 6 is a diagram illustrating an example of the dense/striated region extraction processing according to the present embodiment. The dense/striated region extraction processing illustrated in FIG. 6 corresponds to Step S140 illustrated in FIG. 2.

Figure 7:
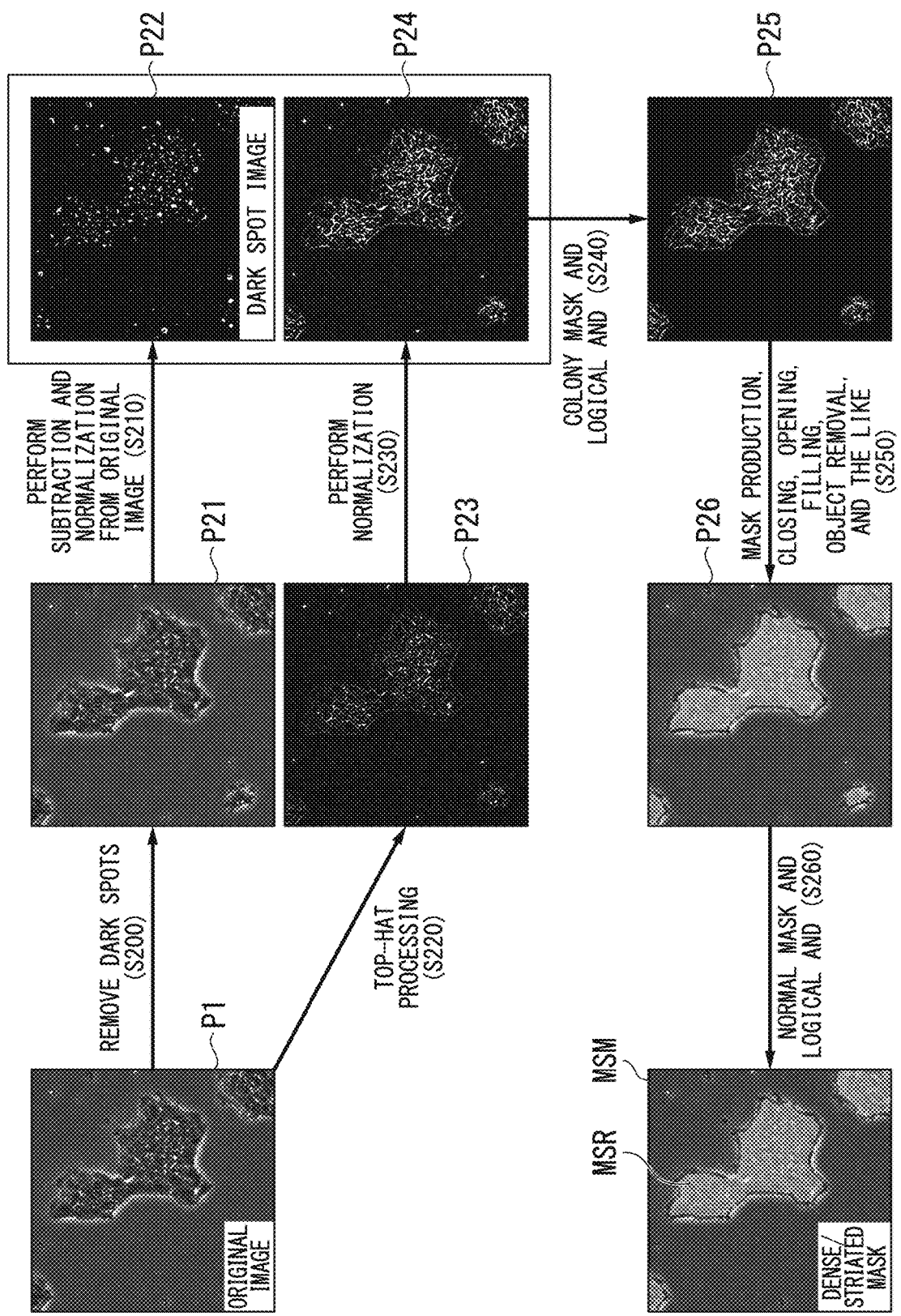
FIG. 7 is a diagram illustrating an example of an image generated in each kind of processing included in the dense/striated region extraction processing according to the first embodiment of the present invention.

FIG. 7 is a diagram illustrating an example of an image generated in each kind of processing included in the dense/striated region extraction processing according to the present embodiment.

Step S200: The dense/striated mixture region extraction unit 12 removes dark spots from the phase contrast image P1 acquired by the phase contrast image acquisition unit 10. The dense/striated mixture region extraction unit 12 generates a dark spot removed image P21 as a result of removing the dark spots from the phase contrast image P1. Here, the dark spots are regions in which luminance of pixels is lower than a predetermined value in the phase contrast image P1. The dark spots correspond mainly to nuclei of the pluripotent stem cells.

Step S210: The dense/striated mixture region extraction unit 12 subtracts luminance of each pixel in the dark spot removed image P21 generated in Step S200 from luminance of each pixel in the phase contrast image P1 and normalizes the luminance. Here, if the luminance of each pixel in the dark spot removed image P21 is subtracted from the luminance of each pixel in the phase contrast image P1, dark sports remain. The dense/striated mixture region extraction unit 12 generates a dark spot image P22 by normalizing the luminance of the remaining dark spots.

Step S220: The dense/striated mixture region extraction unit 12 performs top-hat processing on the phase contrast image P1 acquired by the phase contrast image acquisition unit 10. The dense/striated mixture region extraction unit 12 generates a top-hat processing image P23 as a result of performing the top-hat processing on the phase contrast image P1.

Here, the top-hat processing is processing of extracting a region where luminance of pixels is relatively high in the phase contrast image P1. A region where density is high in the regions in the surroundings of the nuclei of the pluripotent stem cells captured in the phase contrast image P1 and the striated region SR are extracted in the top-hat processing.

Step S230: The dense/striated mixture region extraction unit 12 normalizes luminance of each pixel in the top-hat processing image P23 generated in Step S220. The dense/striated mixture region extraction unit 12 generates a normalized image P24 as a result of the normalization.

Step S240: The dense/striated mixture region extraction unit 12 obtains a logical AND of an added image (not illustrated) obtained by adding the dark spot image P22 generated in Step S210 and the normalized image P24 generated in Step S230 and the colony mask CM. The dense/striated mixture region extraction unit 12 generates a colony mask logical AND image P25 as a result of obtaining the logical AND.

The colony mask logical AND image P25 corresponds to a result obtained by excluding the sparse region PR from the phase contrast image P1. The sparse region PR has lower luminance than the dense region DR and the striated region SR.

Note that the dense/striated mixture region extraction unit 12 may obtain a logical AND of the added image and the normal region mask NM instead of the colony mask CM.

Step S250: The dense/striated mixture region extraction unit 12 generates a mask P26 on the basis of the colony mask logical AND image P25 generated in Step S240. Here, the dense/striated mixture region extraction unit 12 generates the mask P26 by performing known image processing on the colony mask logical AND image P25.

The known image processing is, for example, closing, opening, filling, object removal, and the like. Through the known image processing, a striated pattern in the striated region SR and gaps of cells in the dense region DR are filled, for example, in the colony mask logical AND image P25.

Step S260: The dense/striated mixture region extraction unit 12 obtains a logical AND between the normal region mask NM and the mask P26 generated in Step S250. The dense/striated mixture region extraction unit 12 generates the dense/striated mask MSM as a result of obtaining the logical AND. The dense/striated mixture region extraction unit 12 supplies the generated dense/striated mask MSM to the sparse region extraction unit 13, the striated region extraction unit 14, and the dense region extraction unit 15.

Returning to FIG. 2, description of the extraction processing of the image processing device 1 will be continued.

Step S150: The sparse region extraction unit 13 extracts the sparse region PR on the basis of the dense/striated mask MSM generated by the dense/striated mixture region extraction unit 12 and the normal region mask NM generated by the normal region extraction unit 112. Here, the sparse region extraction unit 13 extracts the sparse region PR by subtracting the dense/striated mask MSM from the normal region mask NM.

The sparse region extraction unit 13 generates the sparse mask PM as a result of extracting the sparse region PR. The sparse region extraction unit 13 supplies the generated sparse mask PM to the output unit 16.

Figure 8:
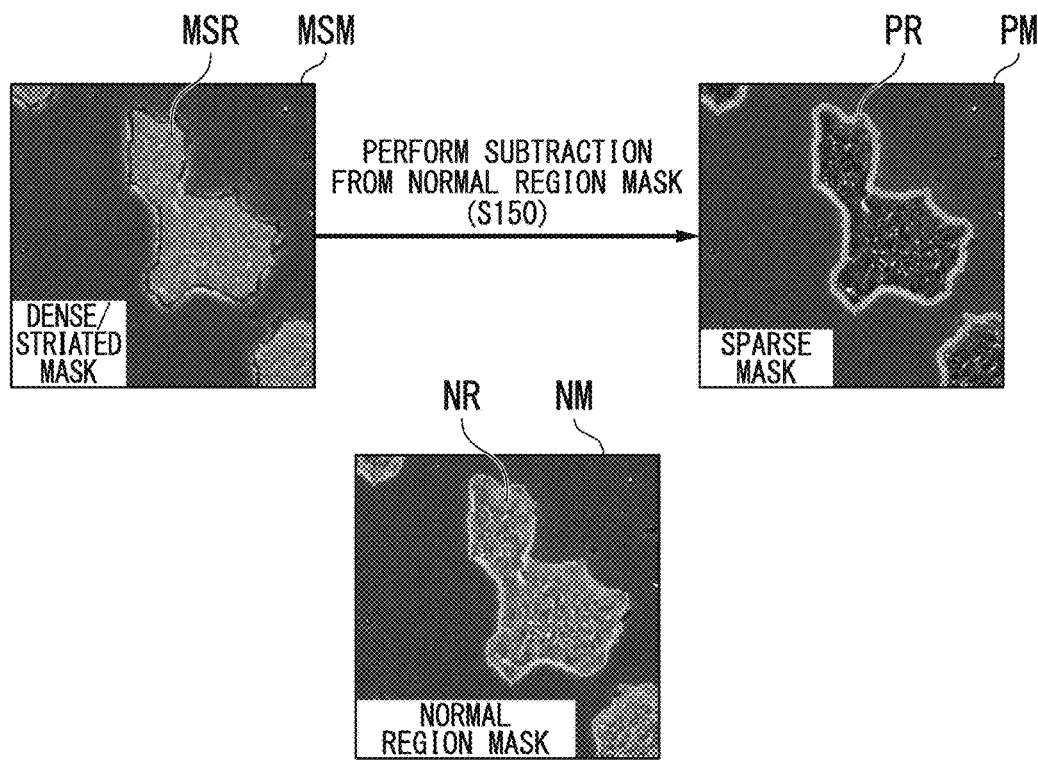
FIG. 8 is a diagram illustrating an example of a sparse mask generated in sparse region extraction processing according to the first embodiment of the present invention.

Here, FIG. 8 illustrates the sparse mask PM generated as a result of the sparse region extraction processing in Step S150.

FIG. 8 is a diagram illustrating an example of the sparse mask PM generated in the sparse region extraction processing according to the present embodiment.

Note that in Step S150, the sparse region extraction unit 13 may extract the sparse region PR on the basis of the colony mask CM generated by the extraction unit 110 and the dense/striated mask MSM generated by the dense/striated mixture region extraction unit 12 instead of the normal region mask NM. In the case in which the sparse region extraction unit 13 extracts the sparse region PR on the basis of the colony mask CM instead of the normal region mask NM, extraction precision in the sparse region PR may decrease as compared with the case in which the sparse region extraction unit 13 extracts the sparse region PR on the basis of the normal region mask NM.

Returning to FIG. 2, the extraction processing of the image processing device 1 will be continued.

Step S160: The striated region extraction unit 14 extracts the striated region SR on the basis of the phase contrast image P0 acquired by the phase contrast image acquisition unit 10 and the dense/striated mask MSM generated by the dense/striated mixture region extraction unit 12.

Here, striated region extraction processing that is processing in which the striated region extraction unit 14 extracts the striated region SR will be described with reference to FIGS. 9 and 10.

Figure 9:
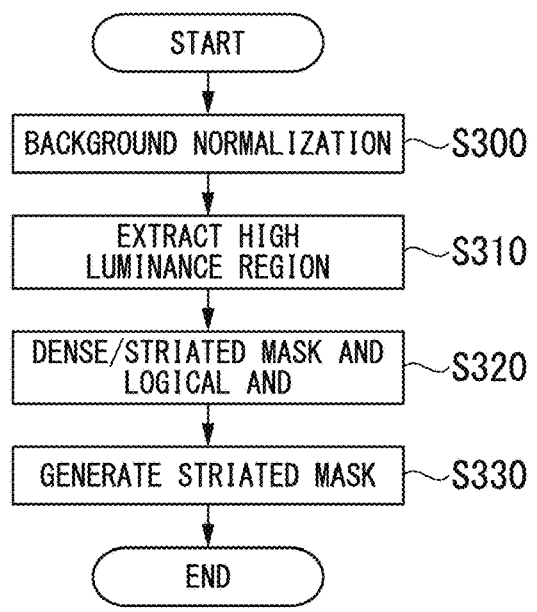
FIG. 9 is a diagram illustrating an example of striated region extraction processing according to the first embodiment of the present invention.

FIG. 9 is a diagram illustrating an example of the striated region extraction processing according to the present embodiment. The striated region extraction processing illustrated in FIG. 9 corresponds to Step S160 illustrated in FIG. 2.

Figure 10:
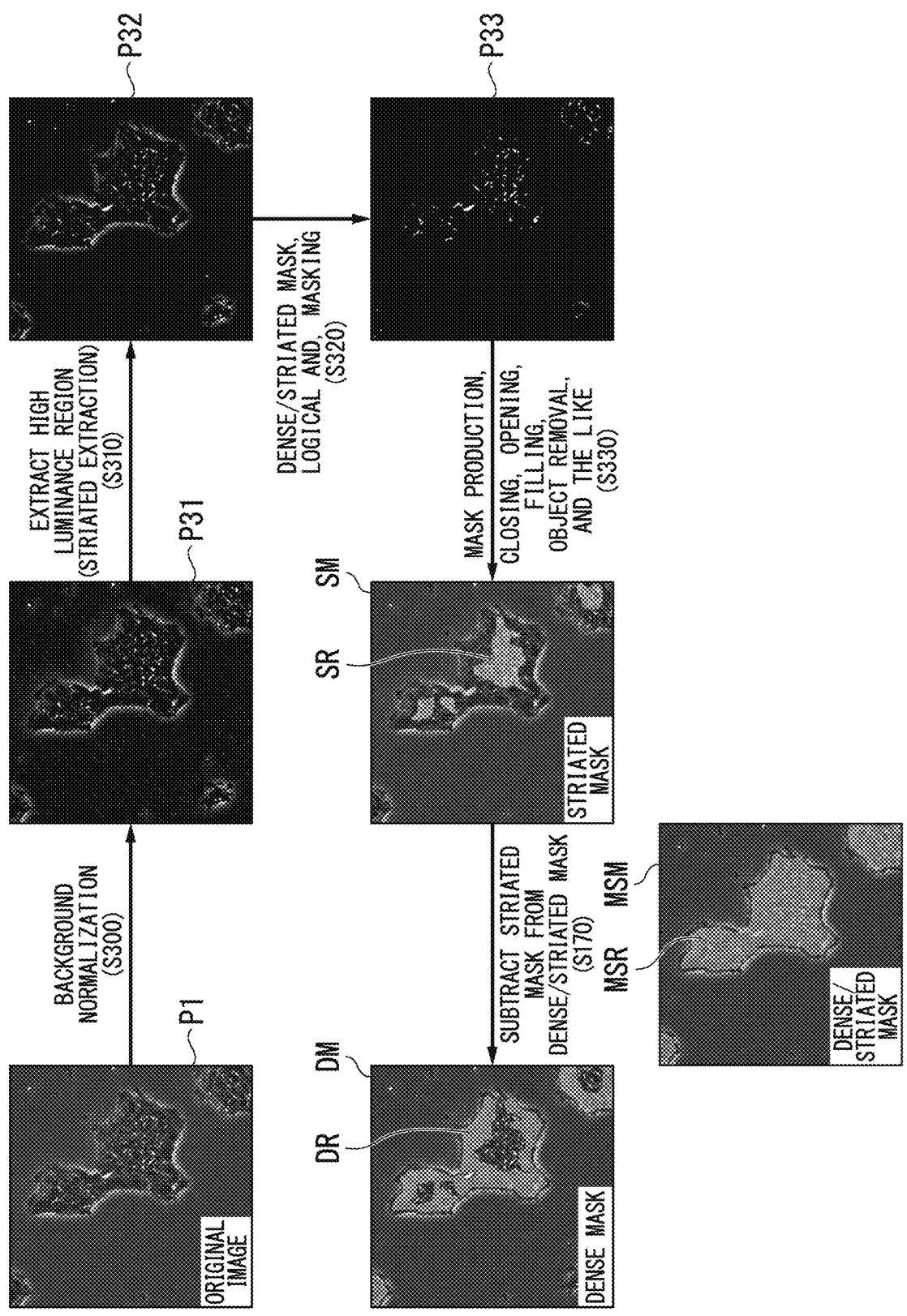
FIG. 10 is a diagram illustrating an example of an image generated in each kind of processing included in the striated region extraction processing according to the first embodiment of the present invention.

FIG. 10 is a diagram illustrating an example of an image generated in each kind of processing included in the striated region extraction processing according to the present embodiment. Note that FIG. 10 also includes an example of an image generated in Step S170 in FIG. 2.

Step S300: The high luminance region extraction unit 140 performs background normalization processing on the phase contrast image P1 acquired by the phase contrast image acquisition unit 10. The high luminance region extraction unit 140 generates a background normalized image P31 as a result of the background normalization processing.

Here, the background normalization is normalizing processing performed such that luminance of each pixel in the phase contrast image P1 falls within a predetermined range. The striated region SR in the phase contrast image P1 is emphasized through the background normalization.

Step S310: The high luminance region extraction unit 140 extracts the high luminance region HR from the background normalized image P31 generated in Step S300. The high luminance region extraction unit 140 generates a high luminance image P32 as a result of the extraction. Here, the high luminance region HR in the background normalized image P31 corresponds to the striated region SR in the phase contrast image P1.

The high luminance region extraction unit 140 supplies the generated high luminance image P32 to the extraction target region extraction unit 141.

Note that the background normalization processing in Step S300 may be omitted. In the case in which the processing in Step S300 is omitted, the high luminance region extraction unit 140 extracts, from the phase contrast image P1, the high luminance region that is a region based on a group of pixels with larger luminance values than the standard value from among the pixels constituting the phase contrast image P1 in Step S310.

Step S320: The extraction target region extraction unit 141 obtains a logical AND between the dense/striated mask MSM generated by the dense/striated mixture region extraction unit 12 and the high luminance image P32 generated by the high luminance region extraction unit 140. The extraction target region extraction unit 141 generates a dense/striated mask logical AND image P33 as a result of obtaining the logical AND.

Here, the dense/striated mask logical AND image P33 corresponds to a result of extracting the striated region SR that is an extraction target region from the phase contrast image P1. In other words, the extraction target region extraction unit 141 extracts the extraction target region from the phase contrast image P1.

The dense/striated mask MSM used by the extraction target region extraction unit 141 to extract the extraction target region is an image generated on the basis of the normal region mask NM in the aforementioned Step S140. Further, the normal region mask NM is the image generated from the colony mask CM in the aforementioned Step S130.

Therefore, the extraction target region extraction unit 141 extracts the extraction target region from the phase contrast image P1 on the basis of the colony region CR extracted by the colony region extraction unit 11 and the high luminance region HR extracted by the high luminance region extraction unit 140.

Step S330: The extraction target region extraction unit 141 generates the striated mask SM on the basis of the dense/striated mask logical AND image P33 generated in Step S320. Here, the extraction target region extraction unit 141 generates the striated mask SM by performing the aforementioned known image processing on the dense/striated mask logical AND image P33.

The extraction target region extraction unit 141 supplies the generated striated mask SM to the dense region extraction unit 15 and the output unit 16.

Returning to FIG. 2, the extraction processing of the image processing device 1 will be continued.

Step S170: The dense region extraction unit 15 extracts the dense region DR by subtracting the striated mask SM generated by the striated region extraction unit 14 from the dense/striated mask MSM generated by the dense/striated mixture region extraction unit 12. The dense region extraction unit 15 generates a dense mask DM as a result of extracting the dense region DR. The dense region extraction unit 15 supplies the generated dense mask DM to the output unit 16.

Here, an example of the dense mask DM is illustrated in FIG. 10.

Step S180: The output unit 16 supplies a processing result PP1 to the presentation unit 3 and causes the presentation unit 3 to output the processing result PP1. The processing result PP1 is an example of the processing result PP and an image in which the striated region SR extracted by the striated region extraction unit 14, the dense region DR extracted by the dense region extraction unit 15, and the sparse region PR extracted by the sparse region extraction unit 13 are indicated respectively in the phase contrast image P1 acquired by the phase contrast image acquisition unit 10. Here, the striated region SR is indicated by the striated mask SM. The dense region DR is indicated by the dense mask DM. The sparse region PR is indicated by the sparse mask PM.

Here, the striated region SR is an extraction target region extracted by the extraction target region extraction unit 141. In other words, the output unit 16 outputs, as an extraction result, the extraction target region extracted by the extraction target region extraction unit 141.

As described above, the image processing device 1 according to the present embodiment includes the colony region extraction unit 11, the high luminance region extraction unit 140, and the extraction target region extraction unit 141.

The colony region extraction unit 11 extracts the colony region CR of the pluripotent stem cell from a microscopic image (the phase contrast image P0 in this example) obtained using transmitted illumination.

The high luminance region extraction unit 140 extracts, from the phase contrast image P0, the high luminance region HR that is a region based on a group of pixels with larger luminance values than the standard value from among pixels constituting the microscopic image (the phase contrast image P0 in this example) obtained using transmitted illumination.

The extraction target region extraction unit 141 extracts, from the microscopic image (the phase contrast image P0 in this example) obtained using transmitted illumination, an extraction target region (the striated region SR in this example) on the basis of the colony region CR extracted by the colony region extraction unit 11 and the high luminance region HR extracted by the high luminance region extraction unit 140.

With this configuration, the image processing device 1 according to the present embodiment can extract the extraction target region (the striated region SR in this example) from the microscopic image (the phase contrast image P0 in this example) obtained using transmitted illumination, and it is thus possible to improve precision of a result of evaluating a maturity level of the colony of the pluripotent stem cells as compared with a case in which the extraction target region (the striated region SR in this example) is not taken into consideration.

Here, the extraction target region (the striated region SR in this example) is the high luminance region HR in the colony region CR included in the microscopic image (the phase contrast image P0 in this example) obtained using transmitted illumination.

Also, in the image processing device 1 according to the present embodiment, the colony region extraction unit 11 extracts, as the normal region NR, a region with surroundings including a portion where the phase contrast is equal to or greater than the predetermined value in the colony region CR.

With this configuration, the image processing device 1 according to the present embodiment can extract the extraction target region (the striated region SR in this example) with the abnormal region AR excluded therefrom, and it is thus possible to improve precision of the result of evaluating the maturity level of the colony of the pluripotent stem cells as compared with a case in which the abnormal region AR is not excluded.

Also, in the image processing device 1 according to the present embodiment, the extraction target region is a region where a striated pattern appears in the microscopic image (the phase contrast image P0 in this example) obtained using transmitted illumination.

With this configuration, the image processing device 1 according to the present embodiment can extract, from the microscopic image (the phase contrast image P0 in this example) obtained using transmitted illumination, the striated region SR corresponding to the transition state between the immature state and the matured state in addition to the sparse region PR corresponding to a state in which the colony is immature and the dense region DR corresponding to a state in which the colony has been matured. It is possible to improve precision of the evaluation when the maturity level of the colony of the pluripotent stem cells is evaluated on the basis of the striated region SR as compared with a case in which the evaluation is made on the basis of only the sparse region PR and the dense region DR.

Although in the aforementioned first embodiment, the "colony mask CM" is defined as a mask image that masks the region other than the colony region CR in the phase contrast image P0, and the "normal region mask NM" is defined as a mask image that masks the region other than the normal region NR in the phase contrast image P0, for example, the "colony mask CM" may be defined as a mask image that masks only the colony region CR, and the "normal region mask NM" may be defined as a mask image that masks only the normal region NR.

Second Embodiment

Hereinafter, a second embodiment of the present invention will be described with reference to the drawings.

In the aforementioned first embodiment, the case in which the image processing device extracts the striated region from the phase contrast image has been described. In the present embodiment, a case in which a phase contrast image is a time lapse image and an image processing device presents an indicator regarding culture on the basis of a temporal change in area of a striated region will be described.

The image processing device according to the present embodiment will be referred to as an image processing device 1a. A phase contrast image PT according to the present embodiment is a plurality of images of pluripotent stem cells captured at different times.

Figure 11:
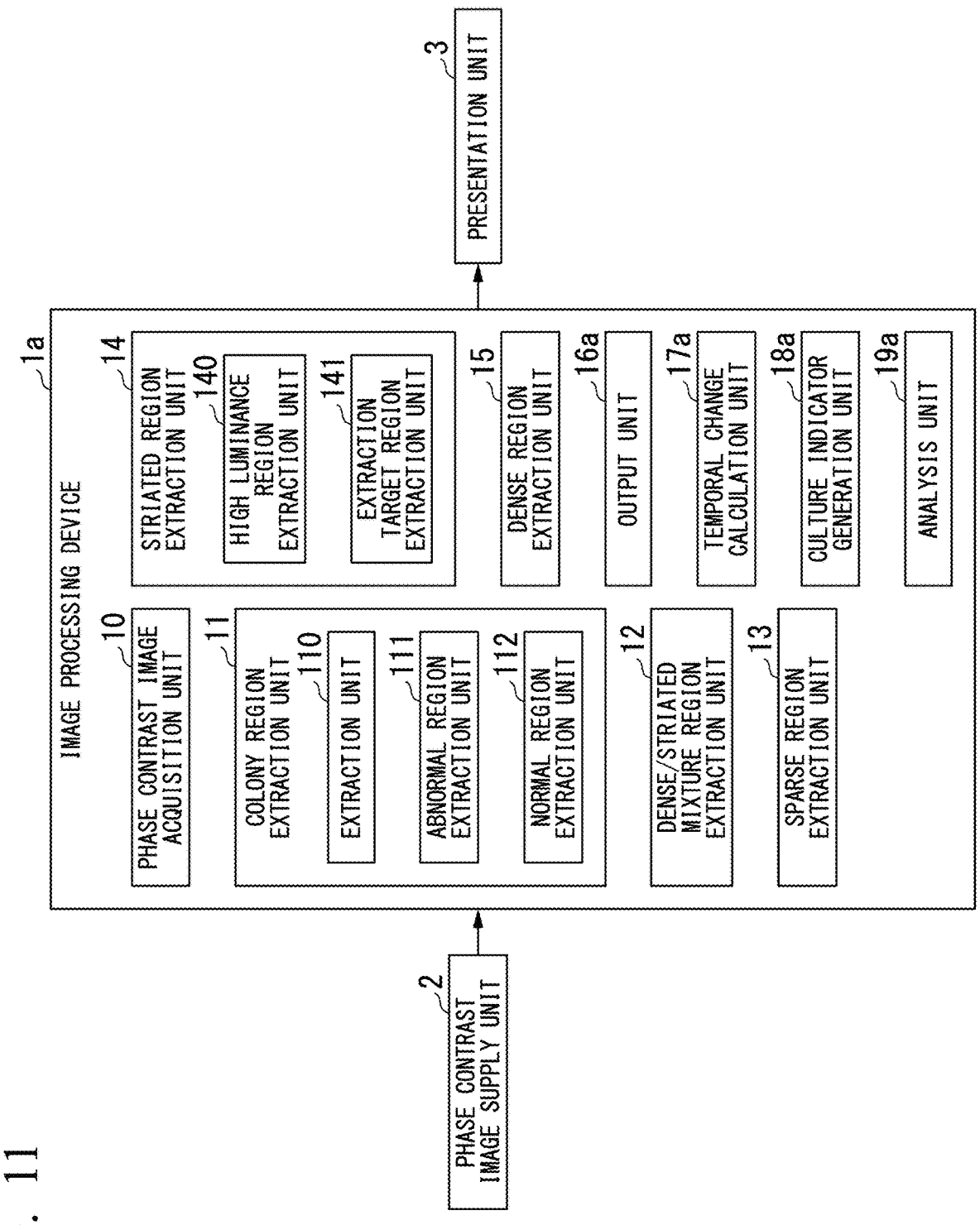
FIG. 11 is a diagram illustrating a configuration of an image processing device according to a second embodiment of the present invention.

FIG. 11 is a diagram illustrating a configuration of an image processing device 1a according to the present embodiment. If the image processing device 1a (FIG. 11) according to the present embodiment and the image processing device 1 (FIG. 1) according to the first embodiment are compared, an output unit 16a, a temporal change calculation unit 17a, a culture indicator generation unit 18a, and an analysis unit 19a are different. Here, functions that the other components (the phase contrast image acquisition unit 10, the colony region extraction unit 11, the dense/striated mixture region extraction unit 12, the sparse region extraction unit 13, the striated region extraction unit 14, and the dense region extraction unit 15) have are the same as those in the first embodiment. A description of the same functions as those in the first embodiment will be omitted, and parts different from those in the first embodiment will be mainly described in the second embodiment.

The temporal change calculation unit 17a calculates a temporal change in proportion of the areas of the sparse region PR, the striated region SR, and the dense region DR occupy the colony region. In the present embodiment, the normal region NR is defined as an example of the colony region. Here, the phase contrast images PT include one or more normal regions NR.

The culture indicator generation unit 18a generates, for each normal region NR, an indicator regarding culture on the basis of the temporal change calculated by the temporal change calculation unit 17a. Hereinafter, the indicator regarding culture will be referred to as a culture indicator CI. The culture indicator CI indicates, for example, "passage", "culture continuation", and "discarding".

The analysis unit 19a analyzes the normal region NR included in the phase contrast images PT on the basis of the culture indicator CI generated by the culture indicator generation unit 18a.

The output unit 16a outputs an analysis result A obtained by the analysis unit 19a to the presentation unit 3 and causes the presentation unit 3 to display the analysis result A.

Figure 12:
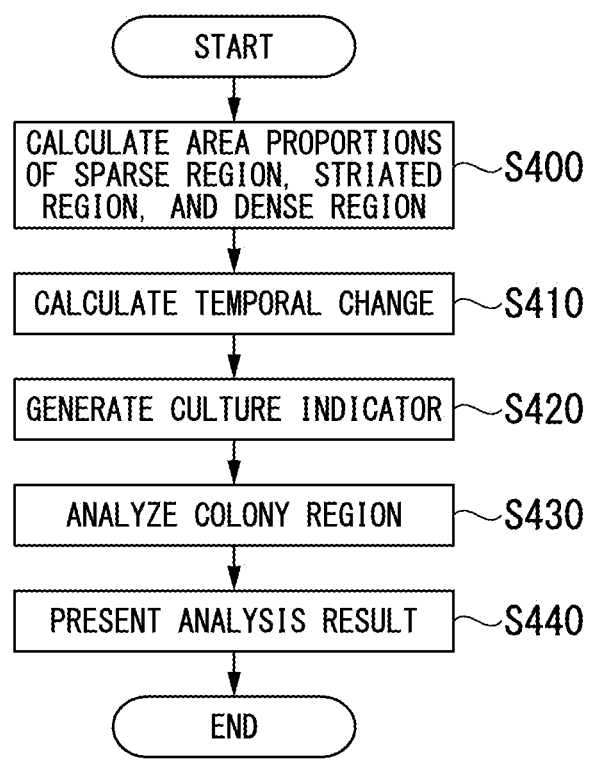
FIG. 12 is a diagram illustrating an example of culture indicator generation processing of the image processing device according to the second embodiment of the present invention.

FIG. 12 is a diagram illustrating an example of processing of generating the culture indicator CI of the image processing device 1a according to the present embodiment. The image processing device 1a executes the processing of generating the culture indicator CI (FIG. 12) after the extraction processing in the first embodiment (FIG. 2) is completed.

Step S400: The temporal change calculation unit 17a calculates a proportion of each of areas of the sparse region PR, the striated region SR, and the dense region DR occupying the normal region NR for each normal region NR. Note that the temporal change calculation unit 17a may calculate each of the areas of the sparse region PR, the striated region SR, and the dense region DR.

Step S410: The temporal change calculation unit 17a calculates, for each normal region NR, each of temporal changes in the aforementioned area proportions of the sparse region PR, the striated region SR, and the dense region DR in a phase contrast images PT0. The temporal change calculation unit 17a may calculate each of the temporal changes in areas of the sparse region PR, the striated region SR, and the dense region DR.

Here, the normal region NR is extracted by the extraction unit 110 of the colony region extraction unit 11. Also, the striated region SR is an extraction target region extracted by the extraction target region extraction unit 141.

In other words, the temporal change calculation unit 17a calculates a temporal change in area of the extraction target region occupying the colony region (normal region NR).

Step S420: The culture indicator generation unit 18a generates, for each normal region NR, the culture indicator CI on the basis of the temporal change calculated in Step S410.

In other words, the culture indicator generation unit 18a generates an indicator regarding culture on the basis of the temporal change calculated by the temporal change calculation unit 17a.

The present inventors have found that if a colony of pluripotent stem cells is cultured from an immature state to a matured state, the proportion of the area of the striated region SR occupying the area of the entire normal region NR increases and decreases once, and there is substantially no striated region SR at last.

Therefore, the culture indicator generation unit 18a may generate a culture indicator CI indicating "culture continuation" in a case in which the area proportion of the striated region SR is higher than a predetermined value, for example. In a case in which the area proportion of the striated region SR is higher than the predetermined value, the state is considered to be a transition state, and it is thus preferable to continue the culture without performing passage.

Also, in a case in which the area proportion of the striated region SR increases, then decreases, and falls below the predetermined value, for example, the culture indicator generation unit 18a may generate the culture indicator CI indicating "passage". Such a colony is evaluated to have been sufficiently matured and can be subject to passage.

The culture indicator generation unit 18a generates a culture indicator CI indicating "passage" in a case in which the area proportion of the striated region SR is equal to or less than the predetermined value and the area proportion of the dense region DR is higher than the area proportion of the sparse region PR, for example. A colony in which the area proportion of the striated region SR is equal to or less than a predetermined value and the area proportion of the dense region DR is higher than the area proportion of the sparse region PR is considered to be in a mature state, it is preferable to perform passage. On the other hand, in a case in which it is not possible to extract the striated region SR from a colony, the colony is considered to have not been matured normally, and the culture indicator generation unit 18*a* may thus generate a culture indicator CI indicating "discarding".

Step S430: The analysis unit 19*a* analyzes each normal region NR included in the phase contrast images PT on the basis of the culture indicator CI generated by the culture indicator generation unit 18*a*. The analysis unit 19*a* supplies the analysis result A to the output unit 16.

The analysis unit 19*a* extracts the normal region NR with a culture indicator CI indicating "passage" as a colony for which passage is possible, for example.

The analysis unit 19*a* makes determination of "culture continuation" for a vessel where the pluripotent stem cell captured in the phase contrast images PT is cultured in a case in which the proportion of the normal region NR with the culture indicator CI indicating "culture continuation" is equal to or greater than a predetermined proportion in the phase contrast images PT, for example.

The analysis unit 19*a* makes determination of "discarding" for a vessel where the pluripotent stem cell captured in the phase contrast images PT is cultured in a case in which the proportion of the normal region NR with the culture indicator CI indicating discarding is equal to or greater than a predetermined proportion in the phase contrast images PT, for example.

Step S440: The output unit 16*a* supplies the analysis result A obtained by the analysis unit 19*a* to the presentation unit 3 and causes the presentation unit 3 to output the analysis result A. The output unit 16*a* causes the presentation unit 3 to present a colony for which passage is possible in a single image corresponding to an imaging time in the phase contrast images PT on the basis of the analysis result A. Also, the output unit 16*a* causes the presentation unit 3 to present a massage such as "culture continuation" or "discarding" for a vessel where the pluripotent stem cell captured in the phase contrast images PT is cultured on the basis of the analysis result A.

Here, an example of area proportions of the sparse region PR, the striated region SR, and the dense region DR occupying the normal region NR will be described with reference to FIG. 13.

Figure 13:
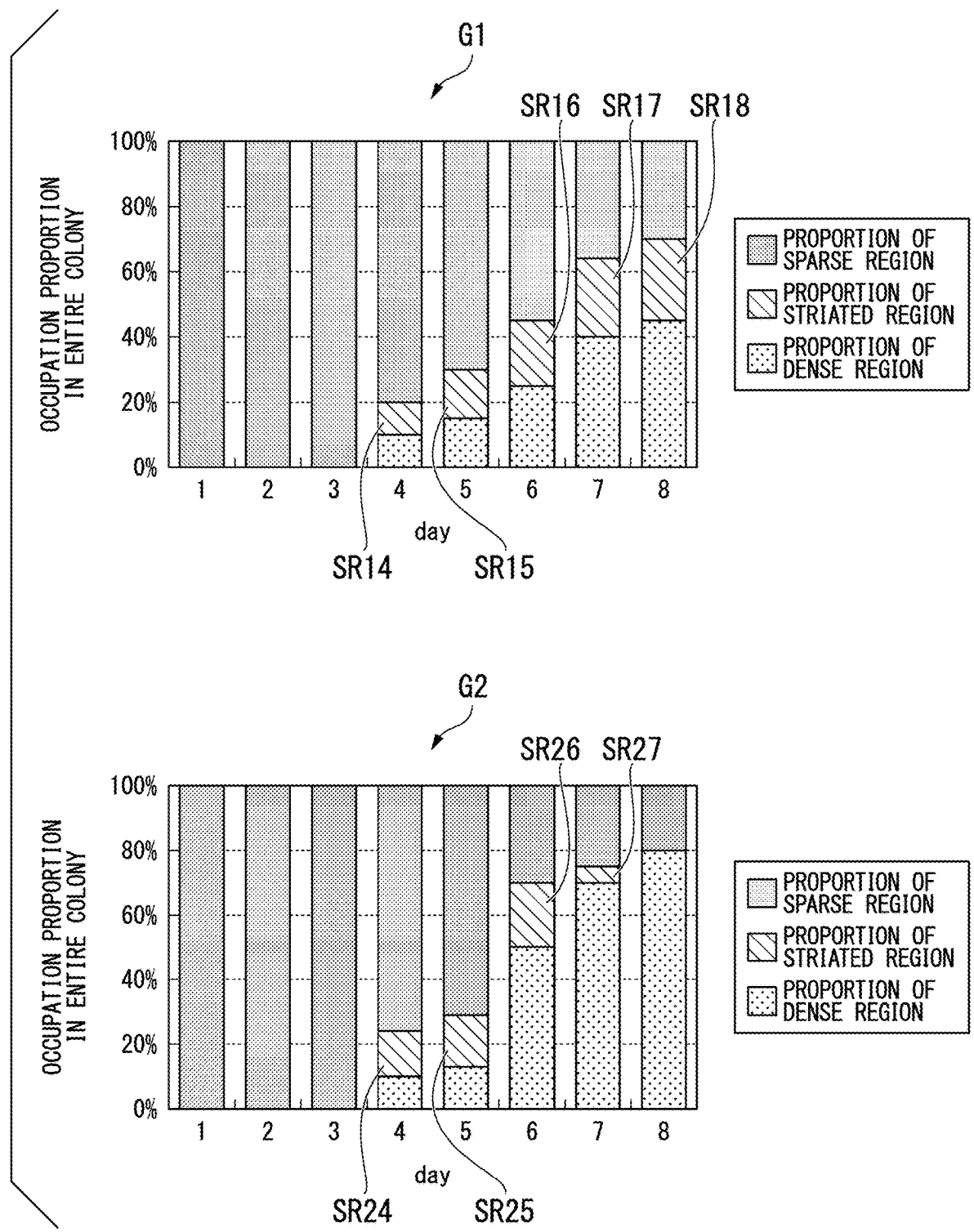
FIG. 13 is a diagram illustrating an example of an area proportion of a sparse region, a striated region, and a dense region occupying a colony region according to the second embodiment of the present invention.

FIG. 13 is a diagram illustrating an example of the area proportions of the sparse region PR, the striated region SR, and the dense region DR occupying the normal region NR according to the present embodiment. A first graph G1 illustrates an example of temporal changes in area proportions of the sparse region PR, the striated region SR, and the dense region DR occupying a certain normal region NR1 which is included in a phase contrast image PT1 captured at a certain timing. A second graph G2 illustrates an example of temporal changes in area proportions of the sparse region PR, the striated region SR, and the dense region DR occupying a certain normal region NR2 which is included in a phase contrast image PT2 captured at a certain timing.

From the first graph G1, a fourth day striated region proportion SR14 and a seventh day striated region proportion SR17 can be seen. From the first graph G1, the striated region proportions on the fourth day and the seventh day are still high, and determination of "culture continuation" is made for a normal region NR1 captured in the phase contrast image PT1.

From the second graph G2, it is possible to see that a fourth day striated region proportion SR24, a fifth day striated region proportion SR25, and a sixth day striated region proportion SR26 increase in this order and a seventh day striated region proportion SR27 is smaller than the sixth day striated region proportion SR26. On the eighth day, the proportion of the striated region SR in the normal region NR2 is substantially zero.

From the second graph G2, determination of "culture continuation" is made for the sixth day and the seventh day, for example, and determination of "passage" is made for the eighth day for a normal region NR2 captured in the phase contrast image PT2.

Here, a case in which the normal region NR is analyzed on the basis of only the sparse region PR and the dense region DR will be described for comparison with the present embodiment.

Figure 14:
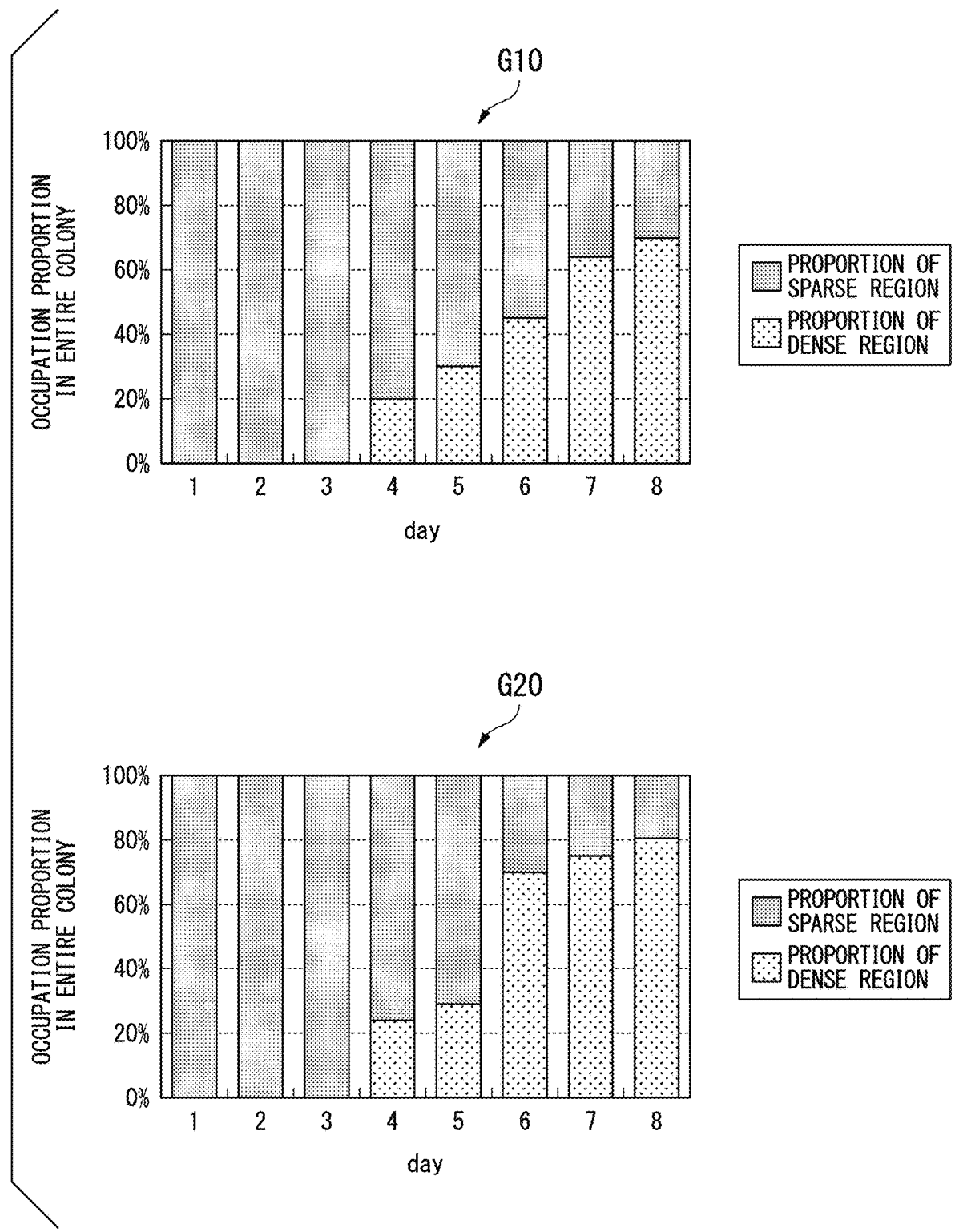
FIG. 14 is a diagram illustrating an example of an area proportion of a sparse region and a dense region occupying a colony region in the related art.

FIG. 14 is a diagram illustrating an example of area proportions of the sparse region PR and the dense region DR occupying the normal region NR. The striated region is included as a part of the dense region DR, and the area proportion of the striated region itself is not calculated. A first graph G10 indicates an example of temporal changes in area proportions of the sparse region PR and the dense region DR occupying a certain normal region NR1 which is included in the same phase contrast image PT1 as that of the first graph G1 in FIG. 13. A second graph G20 indicates an example of temporal changes in area proportions of the sparse region PR and the dense region DR occupying a certain normal region NR2 which is included in the same phase contrast image PT2 as that of the second graph G2 in FIG. 13.

From the first graph G10, determination of "culture continuation" is made for the fourth day, and determination of "passage" is made for the seventh day for the normal region NR1 captured in the phase contrast image PT1. In a case in which the area proportion of the dense region DR is equal to or greater than 60%, for example, the colony is in a matured state, and determination of "passage" is made.

The determination result for the seventh day in FIG. 14 is "passage" while the determination result for the seventh day in the present embodiment is "culture continuation". Since the area proportion of the striated region SR1 is evaluated in the present embodiment, precision of the result of evaluating the maturity level of the colony is higher than that in the related art.

From the seventh graph G20, determination of "passage" is made for the sixth day, the seventh day, and the eighth day for the normal region NR2 captured in the phase contrast image PT2.

The determination results for the sixth day and the seventh day in the present embodiment are "culture continuation" while the determination results for the sixth day and the seventh day in FIG. 14 are "passage". Since the area proportion of the striated region SR2 is evaluated in the present embodiment, precision of the result of evaluating the maturity level of the colony is higher than that in the related art.

As described above, in the image processing device 1*a* according to the present embodiment, the microscopic image (the phase contrast images PT in this example) is a plurality of images of a pluripotent stem cell captured at different times, and the image processing device 1*a* according to the present embodiment includes the temporal change calculation unit 17*a* and the culture indicator generation unit 18*a*.

The temporal change calculation unit 17*a* calculates a temporal change in area of an extraction target region (the striated region SR in this example) occupying a colony region (the normal region NR in this example).

The culture indicator generation unit 18*a* generates an indicator (the culture indicator CI in this example) regarding culture on the basis of the temporal change calculated by the temporal change calculation unit 17a.

With this configuration, since the image processing device 1a according to the present embodiment can generate an indicator (the culture indicator CI in this example) regarding culture on the basis of a temporal change in area of the extraction target region (the striated region SR in this example) occupying the colony region (the normal region NR in this example) at the imaging time, it is possible to improve precision of the result of evaluating the maturity level of the colony as compared with a case in which the indicator is not generated on the basis of the temporal change in area of the extraction target region (the striated region SR in this example) occupying the colony region (the normal region NR in this example) at the imaging time.

Note that although the case in which the image processing device 1 extracts a region where a striated pattern appears as an extraction target region has been described in each of the aforementioned embodiments, the image processing device 1 may detect or measure a striated structure including pixels with high luminance.

Here, the striated structure including pixels with high luminance will be described with reference to FIG. 15.

Figure 15:
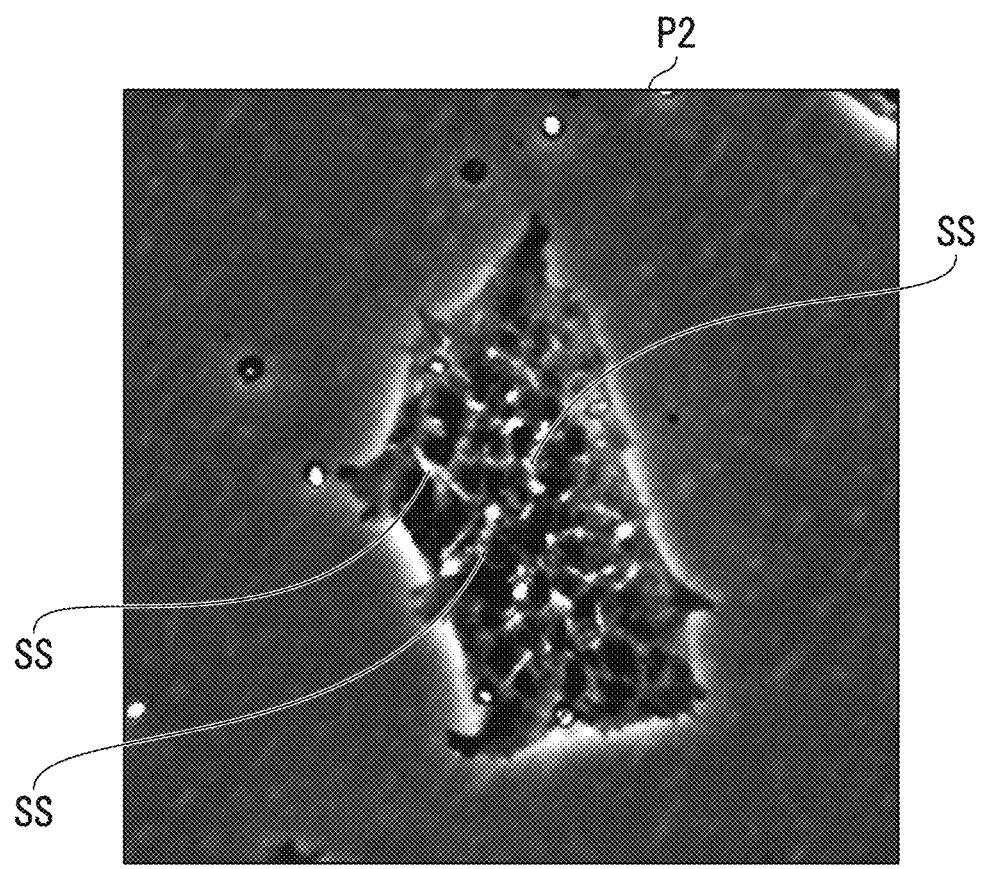
FIG. 15 is a diagram illustrating an example of a striated structure including high luminance pixels according to each embodiment of the present invention.

FIG. 15 is a diagram illustrating an example of a striated structure SS including pixels with high luminance according to each embodiment. The phase contrast image acquisition unit 10 acquires a phase contrast image P2 of a colony of pluripotent stem cells. The striated region extraction unit 14 detects or measure the striated structure SS including pixels with high luminance in the phase contrast image P2 acquired by the phase contrast image acquisition unit 10.

The image processing device 1 evaluates maturity of the colony of the pluripotent stem cells on the basis of the detected or measured striated structure SS.

The image processing device 1 determines that the maturity of the colony of the pluripotent stem cells is a transition state in a case in which the striated structure SS is detected or measured, for example.

In other words, an evaluation method of evaluating the maturity of the colony of the pluripotent stem cells includes an acquisition process of acquiring the phase contrast image P2 of the colony and a detection process of detecting the striated structure SS including the pixels with high luminance in the phase contrast image P2.

Also, the image processing device 1 may detect the striated structure SS including the pixels with high luminance and calculate a temporal change in striated structure SS.

The phase contrast image acquisition unit 10 acquires a plurality of phase contrast images PT20. Here, the plurality of phase contrast images PT20 are phase contrast images of the colony of the pluripotent stem cells captured at different times. The striated region extraction unit 14 detects the striated structure SS in each of the plurality of phase contrast images PT20 acquired by the phase contrast image acquisition unit 10. The temporal change calculation unit 17a calculates a temporal change in striated structure SS detected by the striated region extraction unit 14.

The image processing device 1 evaluates the maturity of the colony of the pluripotent stem cells on the basis of the calculated temporal change in striated structure SS.

In other words, the evaluation method of evaluating the maturity of the colony of the pluripotent stem cells includes an acquisition process of acquiring the plurality of phase contrast images PT20 of the colony captured at different times and the calculation process of detecting the striated structure SS including the pixels with high luminance and calculating the temporal change in striated structure SS for each of the plurality of phase contrast images PT20.

Note that a part of the image processing devices 1 and 1a in the aforementioned embodiments, for example, the phase contrast image acquisition unit 10, the colony region extraction unit 11, the dense/striated mixture region extraction unit 12, the sparse region extraction unit 13, the striated region extraction unit 14, the dense region extraction unit 15, the output unit 16, the temporal change calculation unit 17a, the culture indicator generation unit 18a, and the analysis unit 19a may be realized by a computer. In that case, the part may be realized by recording a program for realizing a control function thereof in a computer readable recording medium and causing a computer system to read and execute the program recorded in the recording medium. Note that the "computer system" described here is a computer system incorporated in the image processing device 1 or 1a and includes hardware such as an OS and peripheral devices. Also, the "computer readable recording medium" means a portable medium such as a flexible disk, a magneto-optic disc, a ROM, or a CD-ROM and a storage device such as a hard disk incorporated in the computer system. Further, the "computer readable recording medium" may include a recording medium that dynamically holds the program for a short time such as a communication line in a case in which the program is transmitted via a network such as the Internet or a communication line such as a telephone line and a recording medium that holds the program for a certain period of time such as a volatile memory inside the computer system that serves as a server or a client in that case. Also, the aforementioned program may realize a part of the aforementioned functions and may be able to realize the aforementioned functions in combination with a program that has already been recorded in the computer system.

Also, a part or entirety of the image processing devices 1 and 1a in the aforementioned embodiments may be realized as an integrated circuit such as a large scale integration (LSI). Each functional block in the image processing devices 1 and 1a may be individually realized as a processor, or a part or entirety thereof may be integrally realized as a processor. Also, the method of forming an integrated circuit is not limited to the LSI and may be realized as a dedicated circuit or a general-purpose processor. Also, in a case in which a technique of forming an integrated circuit that replaces the LSI appears with advancement of semiconductor techniques, an integrated circuit based on the technique may be used.

Although the embodiment of the present invention has been described in detail with reference to the drawings, the specific configuration is not limited to the one described above, and various design modifications and the like may be added without departing from the gist of the present invention.

REFERENCE SIGNS LIST 1, 1a Image processing device
10 Phase contrast image acquisition unit
11 Colony region extraction unit
110 Extraction unit
111 Abnormal region extraction unit
112 Normal region extraction unit
12 Dense/striated mixture region extraction unit
13 Sparse region extraction unit
14 Streak region extraction unit
140 High luminance region extraction unit
141 Extraction target region extraction unit 15 Dense region extraction unit
16, 16a Output unit
17a Temporal change calculation unit
18a Culture indicator generation unit
19a Analysis unit
2 Phase contrast image supply unit
3 Presentation unit

The invention claimed is:

1. An image processing device comprising:
a processor; and
a memory encoded with instructions executed by the processor, the instructions causing the processor to perform operations including:
  imaging pluripotent stem cells over time in a culture process of the pluripotent stem cells and acquiring a plurality of images,
  extracting a colony region of the pluripotent stem cells from an image of the plurality of images,
  extracting, from the image, a high luminance region that is a region based on a group of pixels with larger luminance values than a standard value from among pixels constituting the image,
  extracting an extraction target region with relatively high contrast in the colony region from the image based on the colony region and the high luminance region, and
  outputting the extraction target region as an extraction result,
wherein as a relationship among the colony region, the high luminance region, and the extraction target region, the colony region is formed, the high luminance region is then formed in the colony region, and the extraction target region is then formed in the high luminance region in the culture process of the pluripotent stem cells, and
the extraction target region is a region where a striated pattern appears in the image.

2. The image processing device according to claim 1, wherein
  the operation of extracting the colony region includes extracting, as a normal region, a region with surroundings including a portion where luminance of a boundary is equal to or greater than a predetermined value in the colony region.

3. The image processing device according to claim 1, wherein the instructions cause the processor to perform operations further including
  calculating a temporal change in area occupied by the extraction target region in the colony region, and
  generating an indicator regarding culture based on the temporal change.

4. The image processing device according to claim 1, wherein the extraction target region is a region with relatively high contrast where the striated pattern appears in the colony region.

5. The image processing device according to claim 1, wherein the operation of extracting the high luminance region is an operation in which background normalization processing is performed on a phase contrast image, which is the image, and the high luminance region, which includes a striated region where the striated pattern appears, is extracted on a normalized image on which the background normalization processing has been performed.

6. The image processing device according to claim 1, wherein
  the operation of extracting the colony region is an operation in which a colony mask is generated based on the extracted colony region and a normal region mask is generated based on a normal region obtained by excluding an abnormal region from the colony region,
  the operation of extracting the high luminance region is an operation in which (i) a high luminance region with pixels with relatively high luminance in the image is extracted, (ii) a high luminance region mask that includes a high density region and a striated region in regions surrounding nuclei of the pluripotent stem cells is generated based on an image of the high luminance region, and (iii) a dense/striated mask is generated based on the normal region mask and the high luminance region mask, and
  the operation of extracting the extraction target region is an operation in which the striated region is extracted based on the image and the dense/striated mask acquired.

7. An image processing device comprising:
a processor; and
a memory encoded with instructions executed by the processor, the instructions causing the processor to perform operations including
  imaging pluripotent stem cells over time in a culture process of the pluripotent stem cells and acquiring a plurality of images,
  extracting a colony region of the pluripotent stem cells from an image of the plurality of images,
  extracting, from the image, a focused region that is a region based on a group of pixels with luminance values exceeding a standard value from among pixels constituting the image,
  extracting an extraction target region with relatively high contrast in the colony region from the image based on the colony region and the focused region, and
  outputting the extraction target region as an extraction result,
wherein as a relationship among the colony region, the focused region, and the extraction target region, the colony region is formed, the focused region is then formed in the colony region, and the extraction target region is then formed in the focused region in the culture process of the pluripotent stem cells, and
the extraction target region is a region with relatively high contrast where a striated pattern appears in the colony region.

8. The image processing device according to claim 7, wherein the operation of extracting the focused region includes extracting, from the image, a focused region that is a region based on a group of pixels with larger luminance values than the standard value.

9. The image processing device according to claim 7, wherein
  the operation of extracting the colony region includes extracting, as a normal region, a region with surroundings including a portion where luminance of a boundary is equal to or greater than a predetermined value in the colony region.

10. The image processing device according to claim 7, wherein the instructions cause the processor to perform operations further including
  calculating a temporal change in area occupied by the extraction target region in the colony region, and
  generating an indicator regarding culture based on the temporal change calculated.

11. The image processing device according to claim 7, wherein the operation of extracting the focused region is an operation in which background normalization processing is performed on a phase contrast image, which is the image, and the focused region, which includes a striated region where the striated pattern appears, is extracted based on a normalized image on which the background normalization processing has been performed.

12. The image processing device according to claim 7, wherein the operation of extracting the colony region is an operation in which a colony mask is generated based on the extracted colony region and a normal region mask is generated based on a normal region obtained by excluding an abnormal region from the colony region, the operation of extracting the focused region is an operation in which (i) a focused region with pixels with relatively high luminance in the image is extracted, (ii) a focused region mask that includes a high density region and a striated region in regions surrounding nuclei of the pluripotent stem cells is generated based on an image of the focused region, and (iii) a dense/striated mask is generated based on the normal region mask and the focused region mask, and the operation of extracting the extraction target region is an operation in which the striated region is extracted based on the image and the dense/striated mask acquired.

13. An evaluation method for evaluating maturity of a colony of pluripotent stem cells, the method comprising:

an acquisition process of acquiring a phase contrast image of the colony;

a detection process of detecting a striated structure including pixels with high luminance in the phase contrast image; and an output process of outputting an analysis result of maturity of the colony based on a temporal change in the striated structure detected in the detection process.

14. The evaluation method according to claim 13, wherein the detection process further includes calculating a temporal change in striated structure in each of a plurality of the phase contrast images; and the method further comprises a display process of displaying an analysis result of maturity of the colony based on the temporal change in the striated structure calculated.

* * * * *